(12) United States Patent
Lagarrigue-Charbonnier et al.

(10) Patent No.: US 10,407,708 B2
(45) Date of Patent: Sep. 10, 2019

(54) METHOD AND SYSTEM FOR DETERMINING MICROORGANISM GROWTH

(71) Applicants: bioMérieux, Marcy-l'etoile (FR); Commissariat a L'Énergie Atomique et aux Énergies Alternatives (CEA), Batiment "Le Pondant D" (FR)

(72) Inventors: Marthe Lagarrigue-Charbonnier, Paris (FR); Lorène Allano, Sèvres (FR); Marine Depecker, Morsang-sur-Orge (FR)

(73) Assignees: Commissariat a L'Energie Atomique et aux Energies Alternatives, Paris (FR); Biomerieux, Marcy-L'Etoile (FR)

( * ) Notice: Subject to any disclaimer, the term of this patent is extended or adjusted under 35 U.S.C. 154(b) by 165 days.

(21) Appl. No.: 15/529,114

(22) PCT Filed: Nov. 26, 2015

(86) PCT No.: PCT/FR2015/053221
§ 371 (c)(1),
(2) Date: May 24, 2017

(87) PCT Pub. No.: WO2016/083744
PCT Pub. Date: Jun. 2, 2016

(65) Prior Publication Data
US 2017/0260564 A1    Sep. 14, 2017

(30) Foreign Application Priority Data

Nov. 26, 2014  (FR) ...................................... 14 61533

(51) Int. Cl.
*C12Q 1/04* (2006.01)
*G06K 9/00* (2006.01)
(Continued)

(52) U.S. Cl.
CPC .............. *C12Q 1/04* (2013.01); *G06K 9/0014* (2013.01); *G06T 7/20* (2013.01); *G06T 7/30* (2017.01); *G06T 7/33* (2017.01)

(58) Field of Classification Search
CPC ........ C12Q 2565/629; C12Q 2563/159; C12Q 1/686; C12Q 2537/143; C12Q 1/6827; C12Q 2531/113; C12Q 2535/131; C12Q 1/6816; C12Q 1/6883; C12Q 1/6886; C12Q 2600/172; C12Q 1/04; C12Q 1/6874; C12Q 1/18; C12Q 1/06; C12Q 1/02; A61N 2005/1091; A61N 5/1017; A61N 5/103; A61N 5/1037; A61N 5/1064; A61B 17/154; A61B 17/155; A61B 17/157; A61B 17/158; A61B 17/1666; A61B 17/1675; A61B 17/1703; A61B 17/1746; A61B 17/175; A61B 17/1778; A61B 2017/568; A61B 2034/105; A61B 2034/108; A61B 2034/2065; A61B 34/10; A61B 34/20; A61B 5/4514; A61B 5/4523; A61B 5/4528; A61B 5/4533; A61B 5/055; A61F 2/30756; A61F 2/30942; A61F 2/38; A61F 2/46; B33Y 70/00; B33Y 80/00; Y10T 29/49; G06F 17/30289; G06K 9/0014; G06K 19/06009; G06K 19/06187; G06K 19/067; G06Q 10/06; G06Q 10/10; G06Q 10/107; G06Q 50/18; G06T 2207/10088; G06T 2207/30016; G06T 7/20; G06T 7/30; G06T 7/33; G06T 7/62; G06T 7/0012; G06T 7/11; G06T 7/12; H04L 63/0227; C07K 14/005; C07K 14/47; C07K 14/4747; C07K 14/8121; C07K 16/2803; C07K 19/00; C07K 2317/76; C07K 7/06; C07K 14/415;
(Continued)

(56) References Cited

U.S. PATENT DOCUMENTS 5,510,246 A    4/1996   Morgan

FOREIGN PATENT DOCUMENTS

EP    0796319         9/1997
EP    1061127 A1    12/2000
(Continued)

OTHER PUBLICATIONS

International search report for PCT/FR2015/053221, dated Feb. 8, 2016.
(Continued)

*Primary Examiner* — Deborah K Ware
(74) *Attorney, Agent, or Firm* — Brinks Gilson & Lione

(57) ABSTRACT

Method for determining microorganism growth in a biological sample likely to contain microorganisms, said biological sample being contained in an analysis container, said analysis container being subjected to an incubation of a determined duration, said method comprising:
  acquiring a first plurality of initial images of the analysis container at a first acquisition time T1, before or during the incubation;
  acquiring a second plurality of final images of the analysis container at a second acquisition time T2, during or after the incubation;
  realigning each initial image of the first plurality of initial images acquired, with each corresponding final image of the second plurality of final images acquired;
  locating at least one potential microorganism growth zone in at least one image of the second plurality of images acquired;
  evaluating the content of the potential microorganism growth zone identified in order to determine the presence of microorganisms.

10 Claims, 21 Drawing Sheets

(51) Int. Cl.
*G06T 7/20* (2017.01)
*G06T 7/30* (2017.01)
*G06T 7/33* (2017.01)

(58) Field of Classification Search
CPC .... C07K 16/18; C07K 16/28; C07K 2317/21; C07K 2317/55; C07K 2319/30; C07K 14/39; C07K 14/395; C07K 14/40; C07K 14/70503; C07K 2317/24; C07K 2317/33; C07K 2317/35; C07K 2317/41; C07K 2317/51; C07K 2317/515; C07K 2317/54; C07K 2317/56; C07K 2317/565; C07K 2317/71; C07K 2317/75; C07K 2317/92; C07K 2317/94; C07K 2319/00; C07K 2319/01; C12N 15/1075; C12N 15/111; C12N 15/1131; C12N 15/1132; C12N 2310/14; C12N 2320/11; C12N 2330/10; C12N 2740/16022; C12N 2795/10031; C12N 7/00; C12N 15/8261; C12N 9/0071; C12N 15/8242; C12N 15/8271; C12N 2795/00011; C12N 2795/00031; C12N 15/1138; C12N 15/8223; C12N 15/8229; C12N 15/8245; C12N 15/8273; C12N 2310/111; C40B 50/08; G01N 21/6486; G01N 33/5436; G01N 33/58; G01N 33/5005; G01N 15/1429; G01N 15/1475; G01N 2015/1486; G01N 2015/1488; G01N 2021/6439; G01N 2021/6471; G01N 21/6428; G01N 2333/195; G01N 2333/245; G01N 2333/31; G01N 2333/32; G01N 2333/33; G01N 33/5008; G01N 33/56916; G01N 33/56938; G01N 33/56966; G01N 33/56983; G01N 33/582; G01N 2500/04; G01N 2500/10; G01N 2400/38; G01N 33/50; G01N 33/5082; G01N 33/52; G01N 33/6872; Y02A 90/26; Y02A 40/146; Y04S 10/54; B82Y 10/00; B82Y 20/00; B82Y 5/00; A01N 47/44; A61K 47/6415; A61K 47/60; A61K 31/4745; A61K 38/00; A61K 47/54; A61K 47/542; A61K 47/55; A61K 47/61; A61K 47/64; A61K 47/6903; A61K 47/6921; A61K 47/6935; A61K 47/6939; A61K 2039/505; A61K 39/3955; A61K 45/06; A61K 47/6849; A61K 47/6879; C08G 2210/00; C08G 2650/32; C08G 2650/58; C08G 65/332; C08G 65/333; C08G 65/33331; C08G 65/33337; C08G 65/33396; C08G 65/3342; C08G 65/3344; C08G 65/3348; C08L 2203/02; C12Y 114/11002; C12Y 114/11013; C12M 23/24; C12M 23/34; C12M 23/54; C12M 25/02; C12M 29/04; C12M 21/08; C12M 23/26; C12M 23/50; C12M 35/04; C12M 41/00; C12M 41/26; C12M 41/32; C12M 41/40
See application file for complete search history.

(56) References Cited

FOREIGN PATENT DOCUMENTS

| WO | 1996/018720 | 6/1996 |
|---|---|---|
| WO | 2003/022999 | 3/2003 |
| WO | 2012/152769 | 11/2012 |
| WO | 2014/059357 | 4/2014 |

OTHER PUBLICATIONS

Den Hertog, A.L., et al., "Simplified Automated Image Analysis for Detection Phenotyping of *Mycobacterium tuberculosis* on Porous Supports by Monitoring Growing Microcolonies", PLOS ONE, vol. 5, No. 6 (Jan. 1, 2010), p. E11008.

Chen, Wei-Bang, et al., "An Automated Bacterial Colony Counting Classification System", Information Systems Frontiers; A Journal of Research and Innovation, Kluwer Academic Publishers, vol. 11, No. 4 (Feb. 18, 2009), pp. 349-368.

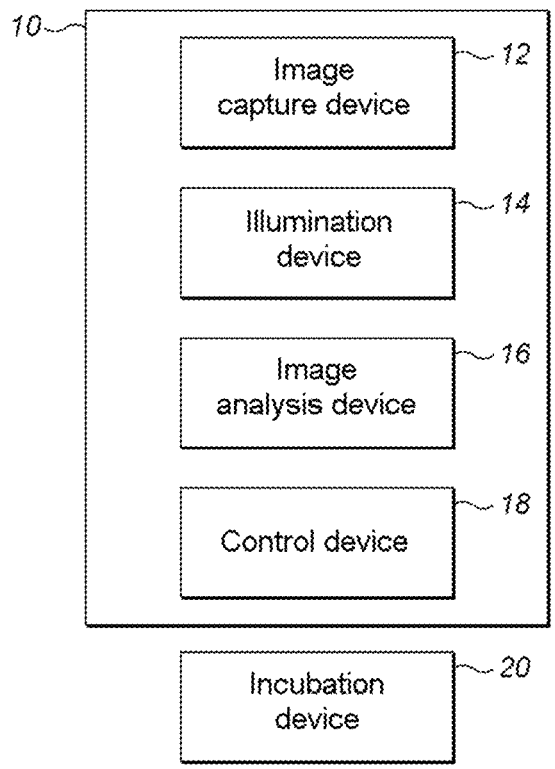
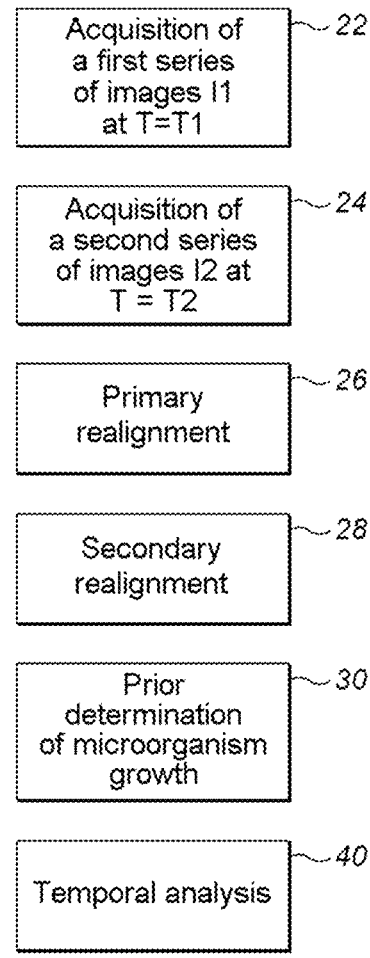
FIG. 1
FIG. 2

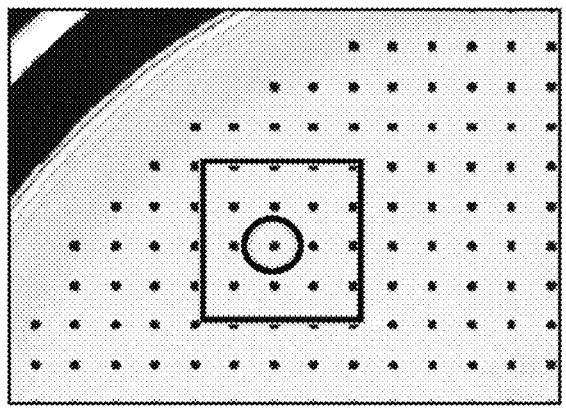
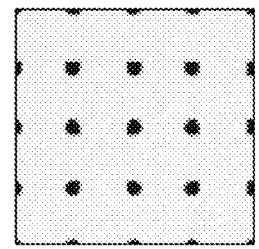
FIG. 22  FIG. 23
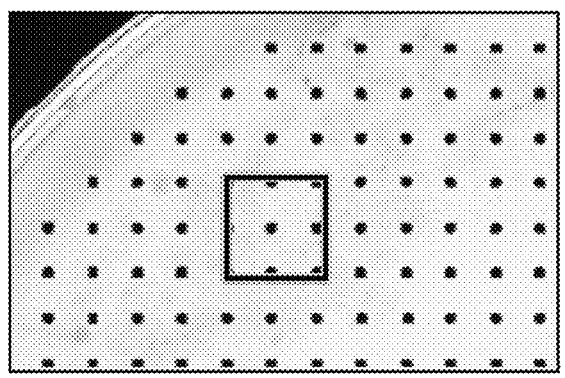
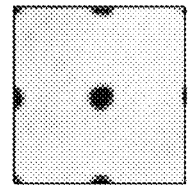
FIG. 24  FIG. 25

METHOD AND SYSTEM FOR DETERMINING MICROORGANISM GROWTH

This application is a National Stage application of International Application No. PCT/FR2015/053221 filed Nov. 26, 2015. This application also claims priority under 35 U.S.C. § 119 to FR Patent Application No. 1461533, filed Nov. 26, 2014.

TECHNICAL FIELD

The invention relates to the field of the processing of images produced by computer, and, more specifically, a method, a system and a computer program product for determining microorganism growth in order to detect and identify microorganisms in an object such as a Petri dish, after the incubation of said object.

STATE OF THE ART

In the field of microbiology, it is known practice to use images of a Petri dish acquired at different incubation times in order to detect and identify any microorganisms. The Petri dish contains a culture medium such as a specific agar in which a sample matched to said agar is seeded. As is known, a first image of the Petri dish is acquired at an instant T0, prior to the incubation of the Petri dish and by means of a suitable imaging system. Thus, the first image acquired has no colony of microorganisms. The Petri dish is then incubated for a determined period of time, until an instant T1. A second image of the Petri dish is then acquired at the instant T1.

Then, the first image acquired at the time T0 is compared with the image acquired at the time T1, in order to determine whether microorganism colonies have appeared during the incubation period, that is to say whether the seeded sample has generated the growth of microorganism colonies within the Petri dish.

However, the comparison of the images of the Petri dish does not make it possible to reliably detect any presence of microorganism colonies. In fact, many parameters can create an erroneous result of the comparison of the images of the Petri dish.

Regarding the Petri dish itself, various parameters can cause an erroneous detection of the microorganism colonies.

A first parameter relates to the material of the Petri dish. Thus, the Petri dish is produced in a material, such as glass or plastic, which can include defects such as scratches. Depending on the conditions of acquisition of the images of the Petri dish, the scratches may appear on the image of the Petri dish as distinct element. Thus, a scratch may be interpreted, erroneously, as representative of a microorganism growth.

A second parameter relates to the elements associated with the Petri dish. Thus, the Petri dish generally has a screen-printed inscription, for example a number making it possible to identify the origin of the production of the Petri dish. Like the scratches, depending on the conditions of acquisition of the images of the Petri dish, the screen-printed inscription may appear on the image of the Petri dish as distinct element. Thus, a screen-printed inscription may be interpreted, erroneously, as representative of a microorganism growth.

A third parameter relates to the culture medium arranged in the Petri dish, such as the agar. In effect, the agar needed for the cultivation of the sample may contain structural defects. Depending on the conditions of acquisition of the images of the Petri dish, these structural defects such as bubbles or a retraction of the agar may also appear as distinct elements on the image of the Petri dish. Thus, the structural defects may also be interpreted, erroneously, as representative of a microorganism growth.

A fourth parameter relates to the presence of condensation. In effect, during the incubation period, water particles forming condensation may appear on the walls of the Petri dish. Now, during the analysis of the Petri dish, the latter is turned over which may cause water particles to drop onto the agar. Thus, depending on the conditions of acquisition of an image of the Petri dish, said water particles may appear in the form of distinct elements on said image of the Petri dish. Thus, the presence of condensation may also lead to an erroneous interpretation of a microorganism growth.

Finally, a fifth parameter relates to any movements of the Petri dish in translation and/or rotation between the acquisition of the first image at T0 and the acquisition of the second image at T1. These movements generate a shift in the position of the object in the first image acquired relative to the position of said object in the second image acquired. Now, a shift between the images acquired at the instants T0 and T1 means that they cannot be compared by overlay, in order to detect the presence of microorganism colonies.

In the prior art, the patent EP0796319 describes a method for identifying microorganism colonies comprising the acquisition of images of a cultivating device such as a Petri dish or a film called Petrilfilm™. The method comprises steps of realignment of the images acquired by using, as reference position, the center of the cultivating device. The realignment involves only a translational movement of the cultivating device between a first image acquired at a time TO and a second image acquired at a time T1. Consequently, the patent EP0796319 does not describe any realignment step that makes it possible to consider a possible rotational movement of the cultivating device between the two image acquisition times T0 and T1. Furthermore, the image acquisition conditions are such that the conditions of illumination of an image acquired at the time T0 are identical to those of an image acquired at the time T1. Thus, the patent EP0796319 describes steps of comparison of the images comprising the subtraction of the pixels of the image acquired at TO with the pixels of the image acquired at T1 in order to obtain a comparison image comprising resulting pixels whose intensity is possibly representative of a microorganism growth. Consequently, the patent EP0796319 does not describe any image comparison steps suitable for images acquired according to different illumination conditions.

Still in the prior art, the patent U.S. Pat. No. 5,510,246 discloses a method for determining microorganism growth in/on a substantially planar culture device such as a plate of Petrifilm™ type. This method notably comprises preliminary steps of image filtering, more specifically of pixel filtering, in order to obtain a background image stripped of "spurious" pixels. This background image is then used to identify the differences observed between an image of the culture device taken after a certain period of incubation of the culture medium (previously inoculated) and said background image. Even though the patent U.S. Pat. No. 5,510,246 deals, generally, with a method for processing images in order to quantify the microcolonies that have grown on a culture medium present in/on a culture device, it is important to note that U.S. Pat. No. 5,510,246 teaches that the method disclosed in this patent is automated and considered reliable in terms of positioning of the culture device, which renders any image realignment step totally pointless, and also any realignment step necessitated by a rotational movement of the culture device during the image acquisition method.

In the prior art, the international patent application WO 2014/059357 also describes a method for determining growth parameters of cells seeded on an analysis medium such as a glass plate. The method comprises a step of realignment of the images of the analysis support, which notably comprises the use:

- of an algorithm known in the prior art, the "Starmatch" algorithm, which uses a fine transformation matrixes and the grouping together of the objects realigned in a two-dimensional Euclidian space, in order to determine the list of the points of interest in each image and then deduce therefrom the optimum transformation, and
- of a function that is also known, the "Gompertz" function, applied to the data zones of the objects grouped together to determine the microorganism growth zones.

A major drawback with the method that is the object of WO 2014/059357 lies in the obligatory presence of points of interest in an image acquired at an initial time in order to be able to find these points of interest again in an image acquired at a later time. Consequently, the method that is the object of WO 2014/059357 does not make it possible to realign images in the absence of microorganism colonies at an initial time.

The European patent application EP-A-1061127, for its part, discloses a method for identifying microorganisms present in an analysis container such as a Petri dish. The method comprises the taking of two images, one after the other, in order to better determine the outlines and the details of at least one microorganism colony. More specifically, the first image is acquired with a first position of the camera and the second image is acquired with a second position of the camera. The displacement between the first image and the second image is therefore a known displacement (and therefore predictable), that can easily be identified on the images. EP-A-1061127 does not disclose, any more than it suggests, any step of image realignment upon an unplanned/unintended displacement of the analysis container.

Furthermore, the article by DEN HERTOG, A. et al., "Simplified Automated Image Analysis for Detection and Phenotyping of *Mycobacterium tubercolisis* on Porous Supports by Monitoring Growing Microcolonies". *PLos ONE*, (2010). Volume 5, Issue 6, e11008, describes a method for analyzing microorganism growth in a porous aluminum oxide support in strip form. The method allows for an automatic detection of the microorganism colonies while specifically detecting individual micro-colonies in order to monitor them over time and identify them as a function of their growth. The article does not describe any step of realignment relating to a displacement of the analysis support Another publication, namely CHEN W-B. "An automated bacterial colony counting and classification system". *Springer Science+Business Media*, (2009). Published online, Inf Syst Front, 11:349-368, describes a method for automatically counting microorganism colonies in an analysis support which can be a Petri dish. The method comprises the detection of the analysis support, the identification of the colonies, the separation of the aggregated colonies and the determination of the number of colonies. This publication does not disclose any step of realignment based on a displacement of the analysis support Consequently, it is necessary to improve the detection of microorganism growth in an object such as a Petri dish by considering the image realignment linked to a translation and/or to a rotation—that may occur unintentionally—of the Petri dish in the acquisition of the images of the Petri dish at different times.

OBJECT OF THE INVENTION

The present invention aims to at least partially overcome the abovementioned problems.

Thus, a first objective of the invention consists in providing a method for determining microorganism growth in a biological sample likely to contain microorganisms, said biological sample being contained in an analysis container such as a Petri dish, said analysis container being subjected to an incubation of a determined duration, said method comprising the following steps:

- acquiring a first plurality of initial images of the analysis container at a first acquisition time T1, before or during the incubation;
- acquiring a second plurality of final images of the analysis container at a second acquisition time T2, during or after the incubation;
- realigning each initial image of the first plurality of initial images acquired, with each corresponding final image of the second plurality of final images acquired;
- locating at least one potential microorganism growth zone in at least one image of the second plurality of images acquired;
- evaluating the content of the potential microorganism growth zone identified in order to determine the presence of microorganisms.

Advantageously, the realignment step comprises a primary realignment step (also called "rough realignment") associated with an identifier located on the analysis container.

Advantageously, the realignment step comprises a secondary realignment step associated with the content of the analysis container.

As is known to those skilled in the art, the realignment of two images consists in mapping together the real object or objects displayed on each of these two images. The realignment of two images proves particularly useful when a displacement of the image-taking device and/or of the object or objects of interest occurs between the acquisition of the two images.

Advantageously, the step of location of at least one potential microorganism growth zone comprises a step of detection of a high density of microorganism colonies, a step of detection of non-circular microorganism colonies and a step of assignment of a location element to said potential microorganism growth zone.

Advantageously, the step of evaluation of the content of the potential growth zone identified comprises a step of determination of the values of two parameters of change.

Advantageously, the two parameters of change comprise a correlation parameter and a contrast parameter.

Advantageously, according to the invention the step of secondary realignment (also called "fine realignment") comprises the creation of a meshing of a subimages for each initial image and each final image. As is known to those skilled in the art, a "subimage" is understood to be a part of an image, of a size less than that of said image. A "subimage" makes it possible to focus/center the image on a point of interest or a local aspect of the image. The size and/or the position of the subimage (in the image) is/are variable according to the wishes of the operator.

The secondary realignment makes it possible to compensate, accurately, namely to pixel scale, the shift (of translation and/or rotation type) created between the images acquired at T1 and the images acquired at T2. Thus, the subsequent steps of location of at least one potential microorganism growth zone and of evaluation of the content of this potential microorganism growth zone can be performed optimally, while limiting—even eliminating—the impact of the artefacts (such as the presence of a scratch or of a screen-printed inscription on the analysis container, for example on a Petri dish) on the interpretation of the results.

Thus, a second objective of the invention consists in providing a system for determining microorganism growth in a biological sample likely to contain microorganisms, said biological sample being contained in an analysis container such as a Petri dish, said analysis container being subjected to an incubation of a determined duration, said system comprising:

- an image capture device in order to acquire a plurality of images of the object to be analyzed at a first acquisition time T1, before or during the incubation, and at a second acquisition time T2, during or after the incubation;
- an illumination device comprising one or more light sources in order to illuminate the analysis container;
- a control device for controlling the application of the method for determining microorganism growth according to the invention in order to determine the presence of microorganisms.

Thus, a third objective of the invention consists in providing a computer program product comprising software instructions for implementing a method according to the invention when said program is run by a data processor.

BRIEF DESCRIPTION OF THE DRAWINGS

The invention, its functionality, its applications and its advantages will be better understood on reading the present description, given with reference to the figures in which:

FIG. 1 shows a schematic view of an image analysis system according to an embodiment of the invention;

FIG. 2 shows a diagram of the steps of the global method for determining microorganism growth according to an embodiment of the invention;

FIG. 22 shows the representation of a pixel in an initial cell;

FIG. 23 shows in detail the content of the square represented in FIG. 22;

FIG. 24 shows the representation of a pixel in a final cell;

FIG. 25 shows in detail the content of the square represented in FIG. 24;

DETAILED DESCRIPTION OF THE INVENTION

Figure 3:
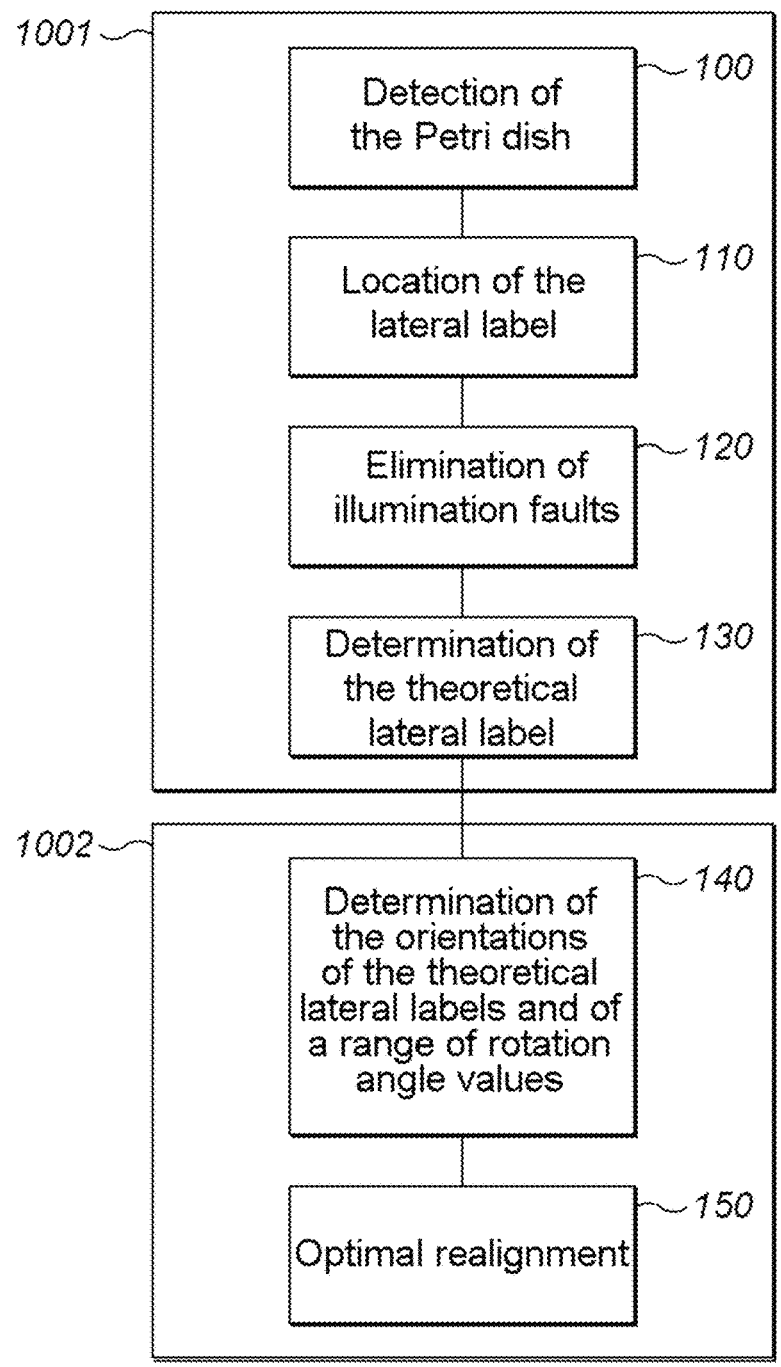
FIG. 3 shows a diagram of the steps of the primary realignment method according to an embodiment of the invention.

The aim of the following detailed description is to explain the invention in a sufficiently clear and comprehensive manner, notably with the aid of examples, but should not in any way be regarded as limiting the scope of the protection to the particular embodiments and to the examples presented hereinbelow.

The present invention relates to the analysis of a sample. According to the present invention, the sample can be of various origins, for example of food, environmental, veterinary, clinical, pharmaceutical or cosmetic origin.

The samples of food origin that can be cited, in a nonexhaustive manner, include a sample of lactose products (yogurts, cheeses, etc.), of meat, fish, egg, fruit, vegetable, water, drink (milk, fruit juice, soda, etc.). Obviously, these samples of food origin may also originate from more elaborate sauces or dishes or from non-transformed or partially transformed raw materials. A food sample may also be derived from a food stuff intended for animals, such as oil cakes, animal meals.

As indicated previously, the sample can be of environmental origin and may consist, for example, of a sampling of surface, of water, of air, etc.

The sample may also consist of a sample of clinical origin, possibly corresponding to samplings of biological fluid (urine, whole blood, or derivatives such as serum, saliva, pus, cerebrospinal liquid, etc.), of salts (for example choleric diarrhea), of samplings of nose, of throat, of skin, of wounds, of organs, of tissues or of isolated cells. This list is of course not exhaustive.

Generally, the term "sample" refers to a part or to a quantity, more particularly a small part or a small quantity, sampled from one or more entities for analysis purposes. This sample may possibly have undergone a prior treatment, involving for example steps of mixing, of dilution or even of grinding, particularly if the original entity is in the solid state.

The sample taken is, generally, likely to contain, or suspected of containing, at least one target external microorganism such as a bacterium, a yeast, a fungus.

According to the present invention, the analysis is performed using an analysis container such as a Petri dish comprising a receptacle and a cover. The receptacle and/or the cover may include an identifier. The receptacle comprises a culture medium such as a culture medium agar. A fluid is seeded on the culture medium before the start of the analysis. The aim of the analysis is to determine the presence of specific microorganisms and the concentration of microorganisms in the fluid on the culture medium, after incubation of the Petri dish.

According to a preferred embodiment of the invention, the analysis container is a Petri dish which comprises, as identifier, a lateral label arranged on the lateral wall of the receptacle of the Petri dish.

According to an embodiment of the invention, the conditions of acquisition of the images of a Petri dish are identical. In this embodiment, the lighting and the angle of view of the Petri dish, in capturing corresponding images at two distinct acquisition times, are identical for each image acquired. According to the present invention, the aim of the analysis of images of a Petri dish is to realign an image acquired before incubation of the Petri dish with a corresponding image acquired after incubation of the Petri dish, or two images of the Petri dish acquired at different incubation times. In effect, in the handling of the Petri dish, using an automated device or by hand, the position of the Petri dish may vary between the instant of acquisition of the image before the incubation and the instant of acquisition of the corresponding image after incubation. Thus, the comparison of the two images acquired at different instants makes it possible to determine the presence or the absence of microorganism colonies located in the Petri dish. Since the Petri dish is circular, the realignment may require a rotation and/or a translation of the image of the Petri dish in order to obtain the match between the two images.

FIG. 1 shows an image analysis system 10 comprising an image capture device 12, an illumination device 14, an image analysis device 16 and a control device 18.

The image capture device 12 comprises a digital device such as a digital camera in order to acquire images of the object to be analyzed. The image capture device 12 acquires a first series of images at a time T1 and a second series of images at a time T2. The time T1 corresponds to an initial instant, that is to say before the seeding of the microorganisms and before translation, or to an initial instant in the presence of microorganisms and after a first period of incubation in the Petri dish. The time T2 corresponds to an instant later than the initial instant T1, after incubation of the Petri dish, or after a second period of incubation, that is to say, potentially, in the presence of microorganisms in the Petri dish. As an example, the image capture device 12 comprises a monochrome image sensor of CCD type consuming between 12 and 24 volts and using the scanning technology with a maximum acquisition rate of 17 images per second.

The illumination device 14 comprises, for example, one or more light sources such as light-emitting diodes (LEDs) in order to illuminate the object to be analyzed according to conditions determined by the user. The light sources are arranged above, or below the Petri dish to be analyzed. The illumination device 14 makes it possible to generate acquisition conditions relating to different possibilities of illumination of the Petri dish such as a red, green and/or blue (RGB) illumination combined with the presence or with the absence a mask situated under the Petri dish, that is to say under the receptacle or under the cover of the Petri dish. Thus, the illumination of "backlight" type corresponds to the acquisition of images in the presence of an illumination behind the Petri dish, in the absence of a mask situated under the Petri dish. The illumination of "bottom annular" or "bottom" type corresponds to the acquisition of images in the presence of an illumination situated above the Petri dish, and according to four directions relative to the Petri dish, that is to say to the left, to the right, to the top part, and to the bottom part of said Petri dish. The illumination of "left bottom" type corresponds to the obtaining of images based on an illumination situated above the Petri dish of "bottom" type and from the left side of said Petri dish. The illumination of "median" type corresponds to the obtaining of a median image based on the four distinct images relating to each direction, left, right, bottom part and top part of the Petri dish, obtained by means of a "bottom" illumination. Other acquisition conditions can be considered by using a combination of light sources arranged according to a specific direction relative to the Petri dish in the presence or in the absence of a mask situated under the Petri dish in order to obtain a visible object without artefacts according to the nature of the sample and of the microorganisms to be identified.

The illumination device 14 can also produce vertical or annular illuminations relative to the Petri dish to be analyzed.

The image analysis device 16 notably comprises an object support and object holding means such as a clamp in order to hold an object such as a Petri dish.

The control device 18 notably comprises a microprocessor (not shown), a display screen (not shown), a storage memory (not shown), in order to execute image processing algorithms. The control device 18 makes it possible to define the operating parameters of the image capture device 12, of the illumination device 14 and of the image analysis device 16, in order to control the operation of the image capture device 12, of the illumination device 14 and of the image analysis device 16.

The image analysis system 10 operates in association with an incubation device 20. The incubation device 20 makes it possible to incubate at least one Petri dish according to specific incubation conditions concerning the duration and temperature in order to promote the growth of microorganisms in the Petri dishes.

Thus, according to a conventional operation, and considering a single Petri dish as an example, the Petri dish seeded with a sample is run via a transport means known from the prior art, such as a transport tape, in the incubation device 20.

At the end of the incubation period, the Petri dish is once again run through the image analysis system 10.

After the processing of the images obtained by means of the image analysis system 10, an identification system (not shown) makes it possible to determine, by a manual or automated method applied to the images acquired, the nature and the number of microorganism colonies which may have developed in the Petri dish.

The present invention relates to the analysis of images available in the image analysis system 10, after incubation of a Petri dish and acquisition of the images of said Petri dish.

In the present invention, by way of example, the object considered is a Petri dish. The present invention applies to a plurality of images or series of images concerning one or more Petri dishes. A first series of images I1 is acquired at a time T=T1 and a second series of images I2 is acquired at a time T=T2. The present description, by way of example, refers to an image I1 from the first series of images I1 acquired at T1 and to an image I2 from the second series of images I2 acquired at T2.

As shown in FIG. 2, the global method according to the present invention comprises a first step of acquisition 22 of the first series of images I1, at a time T1, a second step of acquisition 24 of the second series of images I2, at a time T2, and a step 26 relating to a first primary realignment method, a step 28 relating to a second secondary realignment method, a step 30 relating to a third method of prior detection of microorganisms. In the step 22, the images are acquired according to a method described in the international application published under the number WO2012/152769. The first, second and third methods are distinct and their respective algorithms are stored in the storage memory of the control device 18.

The first method relates to the primary realignment or rough realignment shown in FIG. 3 and relating to the positioning of the Petri dish between the first image I1 acquired at T1 and the second image I2 acquired at T2.

The primary realignment method is based on the detection of the lateral label of the Petri dish. Thus, the primary realignment method comprises, as shown in FIG. 3, a method of detection of the lateral label 1001 and a method of determining primary realignment parameters 1002 associated with the characteristics of the lateral label.

The method of detection of the lateral label 1001 comprises the use of at least two images of the Petri dish, with at least one image acquired by using the "left bottom" illumination condition and at least one image acquired by using the "backlight" illumination condition.

The method of detecting the lateral label 1001 comprises a first step 100 concerning the detection of the Petri dish. The first step 100 comprises a detection of the edges of the Petri dish, according to a method known in the prior art.

The images used in the first step correspond to the images acquired at the time T1 and at the time T2 with the "backlight" illumination condition. Thus, the first step makes it possible to determine the coordinates of the center C and the length of the radius R of the Petri dish, and do so for each image acquired.

In the subsequent steps, only the pixels situated inside a disk characterized by the duly determined values of R and C are considered in the images acquired.

The method of detecting the lateral label comprises a second step 110 concerning the location of the lateral label.

Figure 4:
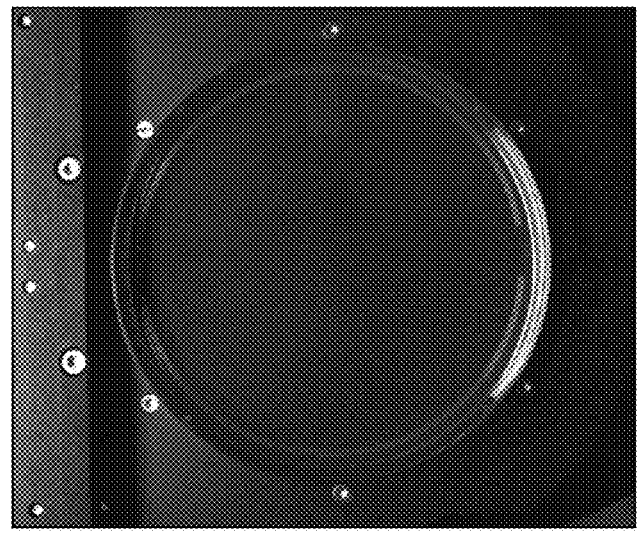
FIG. 4 shows an image of a Petri dish acquired at the time T1.

The images used in the second step 110 correspond to the images acquired at the time T1 as shown in FIG. 4, and at the time T2 with the "left bottom" illumination condition. In effect, the lateral label located on the right side of the Petri dish is visible, optimally, according to this illumination condition.

Figure 5:
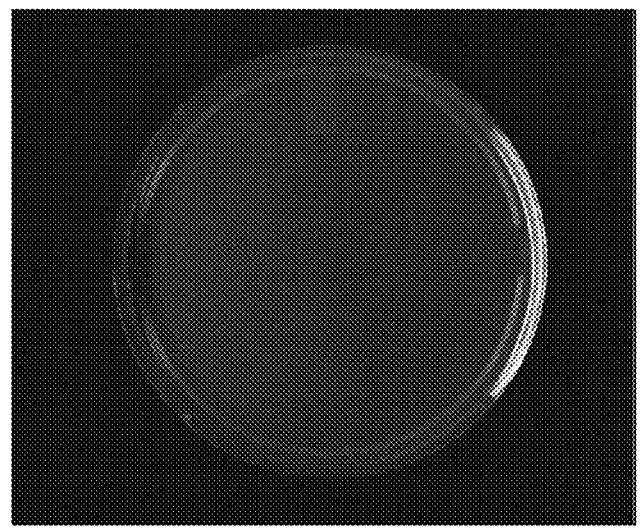
FIG. 5 shows an image of the Petri dish according to FIG. 4 with a representation targeted on the pixels remote from the center of the Petri dish according to a radius R-10 pixels.
Figure 6:
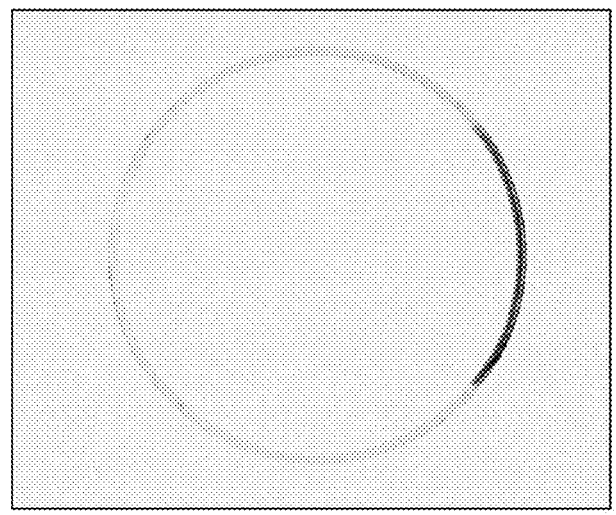
FIG. 6 shows an image of the Petri dish according to FIG. 4 with a representation targeted on the pixels remote from the center of the Petri dish according to a radius R-50 pixels.

The second step 110 comprises the creation of a first disk of radius R1=R−d1 and the creation of a second disk of radius R2=R−d2, d1 and d2 being values determined beforehand by the user, with d1<d2, such that d1=10 pixels and d2=50 pixels. For a Petri dish of radius R=950 pixels, the first disk, as shown in FIG. 5, corresponds to a radius R1=940 pixels and the second disk corresponds to a radius R2=900 pixels. The second step comprises the creation of a resulting ring containing the pixels situated at a distance d lying between R1 and R2, i.e. between 900 and 940 pixels, as shown in FIG. 6.

In the subsequent steps, only the pixels situated inside the resulting ring are considered in the images acquired.

The second step 110 then comprises the application of a segmentation or binarization operation to the image acquired of the Petri dish. In effect, in as much as the lateral label is distinguished by a light portion from the rest of the resulting ring, the segmentation operation makes it possible to effectively isolate the lateral label. The segmentation operation can be used by applying an algorithm such as the k-means algorithm of the Matlab™ software based on a search for two clusters by considering, for one cluster, a centroid initialized at the minimum value of the RGB triplet to approximate the white value and thus group together the light pixels and, for another cluster, a centroid initialized at the maximum value of the RGB triplet to approximate the black value, and thus group together the dark pixels.

Figure 7:
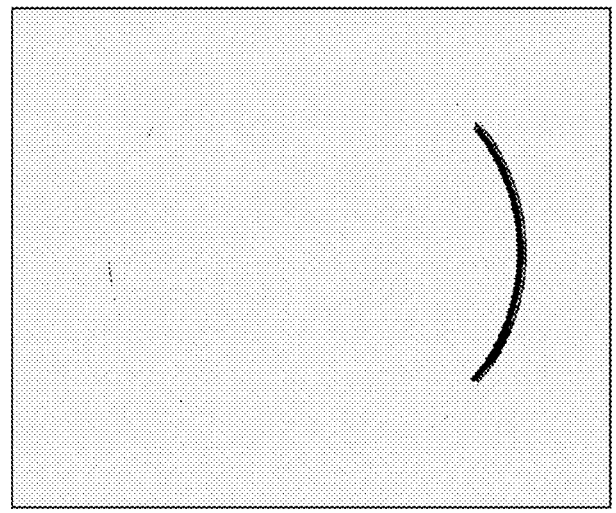
FIG. 7 shows an image of the Petri dish according to the FIG. 4 in application of a segmentation operation.

The segmentation operation makes it possible to identify different objects in the images acquired, as shown in FIG. 7. These objects comprise, for example, the lateral label and reflection defects.

The reflection defects are generated by the reflection of the light beams from the illumination device 14 on the edges of the Petri dish. The light defects or "barbs" have a generally narrow and incurved form.

The lateral label possibly comprises illumination defects relating to an overexposure in the illumination of the Petri dish.

Figure 8:
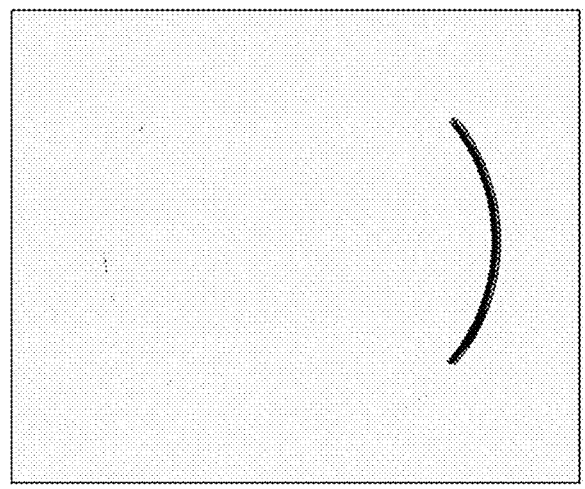
FIGS. 8 and 9 show an image of the Petri dish according to FIG. 4 after the application of a morphological opening operation.
Figure 9:
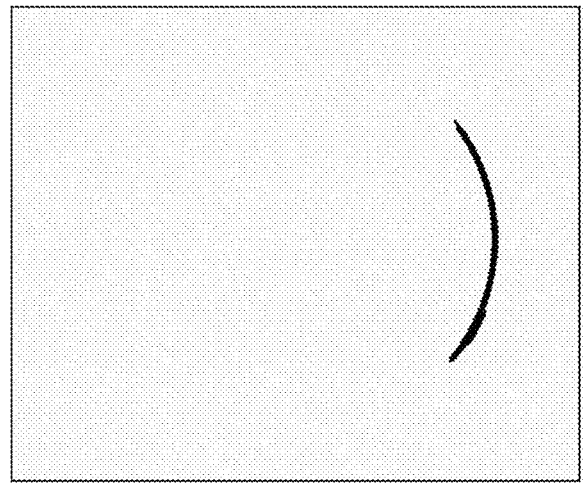
Figure 10:
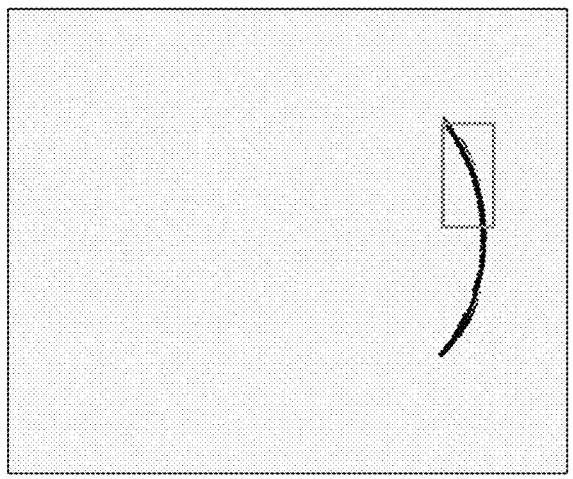
FIG. 10 shows an image of the Petri dish in FIG. 4 after application of an erosion function.
Figure 11:
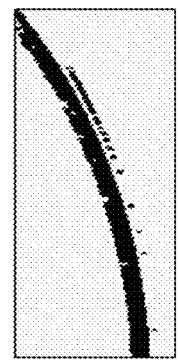
FIG. 11 shows in detail the content of the rectangle represented in FIG. 10.
Figure 12:
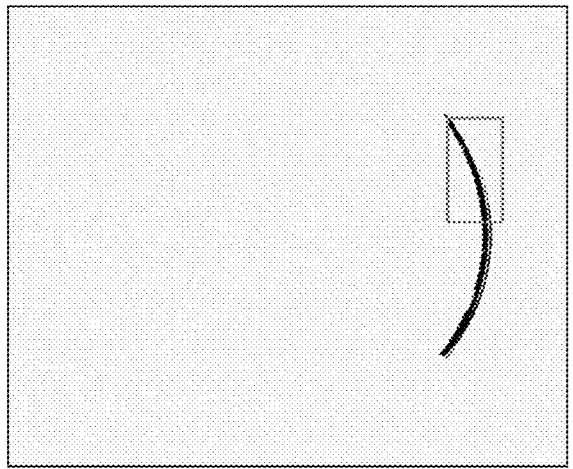
FIG. 12 shows an image of the Petri dish according to FIG. 9 after application of an opening function.
Figure 13:
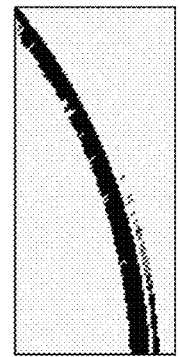
FIG. 13 shows in detail the content of the rectangle represented in FIG. 12.

Generally, the lateral label is formed in a single piece. However, the lateral label may sometimes be made up of different fragments, deliberately or unintentionally. Thus, depending on the type of packaging of the Petri dishes or according to incidents associated for example with the quality of the transport of the Petri dishes, a fragment of the lateral label may prove to be missing. A step of elimination of the illumination defects does not always make it possible to distinguish the lateral label from illumination defects when the size of the lateral label is of the same order of magnitude as the size of the illumination defects. Thus, the method of detecting the lateral label comprises a third step 120 concerning the elimination of the lateral label illumination defects. The third step 120 comprises the application of a morphological opening function, according to the prior art, to the binarized image, shown in FIGS. 8 and 9. The opening function corresponds to the combination of an erosion function and of an expansion function. For the application of the opening function, the STREL function of the Matlab™ software is used in order to define a specific structural element comprising a segment of determined length, for example 10 pixels, concerning a defined number of pixels neighboring the pixel considered, for example 3 pixels, associated with an angle of rotation of said structural element of between −90 and 90 degrees. As shown in FIGS. 10 and 11, the value of the angle of rotation is 0°. As shown in FIGS. 12 and 13, the value of the angle of rotation is 45°.

The erosion function, with the values defined above, makes it possible to eliminate the objects that have a thickness greater than 10 pixels regardless of the curvature of these objects.

The expansion function makes it possible to obtain a correction of the curvature of the lateral label, in order to obtain a global curvature of convex form.

The opening function is applied for each color channel of the RGB triplet.

Thus, on completion of the application of the opening function, the lateral label illumination defects are eliminated on the images at the time T1 and at the time T2.

Then, the method of detecting the lateral label comprises the fourth step 130 relating to the determination of a theoretical lateral label formed in a single fragment. The zone of the Petri dish associated with the theoretical lateral label corresponds to a circular arc of apex situated at the center of the Petri dish, 20 pixels wide and with a spreading angle θ.

The spreading angle θ of the theoretical lateral label is determined by the maximum value θmax and the minimum value θmin of θ in order to define the spread surface covering all of the fragments of the lateral label detected in the preceding step.

Figure 14:
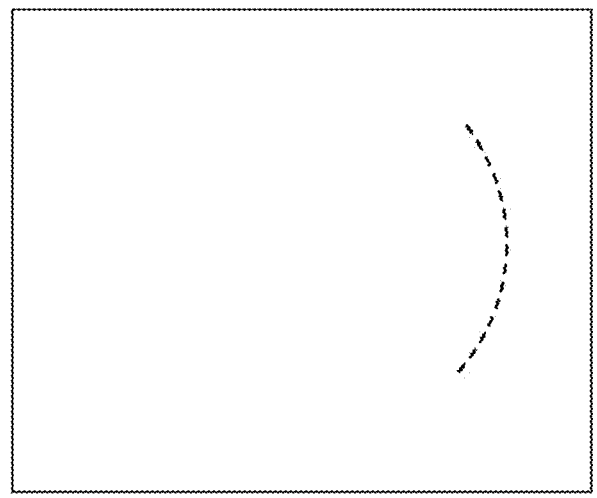
FIG. 14 shows a graphic representation of the theoretical lateral label.

The fourth step 130 makes it possible to obtain a theoretical lateral label, as shown in FIG. 14. The theoretical lateral label is situated on the perimeter of the Petri dish, as shown in FIG. 5, and contains all the fragments of the lateral label.

Thus, the method for determining the primary realignment parameters 1002 can be applied as described below.

The method for determining the primary realignment parameters 1002 comprises a first step 140 concerning the determination of the orientations of the lateral labels and the determination of a range of rotation angle values.

To define a search range for the angle of rotation, the orientation of the theoretical lateral labels at the time T1 and at the time T2 is used.

Figure 15:
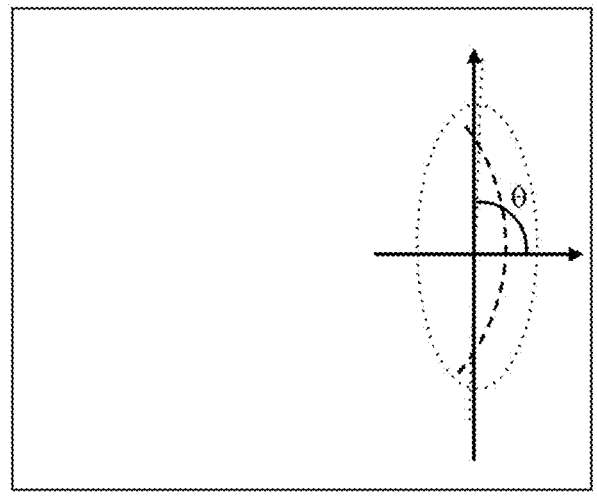
FIG. 15 shows a graphic representation of the theoretical lateral label in discontinuous lines, of the angle of orientation θ in a solid line and of the equivalent ellipsoid in the form of dots.

As is known, the "regionprops" function associated with the "orientation" property of the Matlab™ software makes it possible to determine the orientation of objects in a binarized image. The orientation of the theoretical lateral label is determined by obtaining the angles θ1 and θ2. This orientation corresponds to the orientation of the ellipse having the same moment of inertia as that of the theoretical lateral label, as shown in FIG. 15.

To define the search range for the angle of rotation, the theoretical lateral label is used according to three different aspects.

Figure 16:
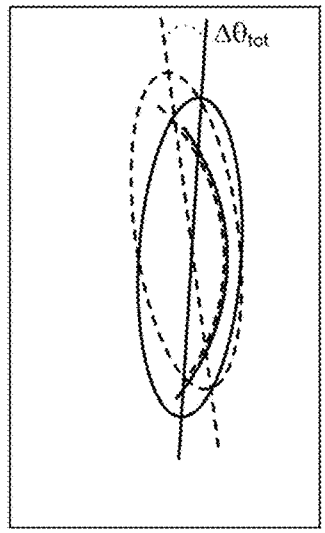
FIG. 16 shows a comparative graphic representation of the images of the lateral label acquired at T1 and at T2.

In effect, according to a first aspect, shown in FIG. 16, the computation of the orientation of the theoretical lateral label is based on all of the theoretical lateral label in order to obtain the corresponding angles θ1tot and θ2tot and the angular deviation Δθtot.

Figure 17:
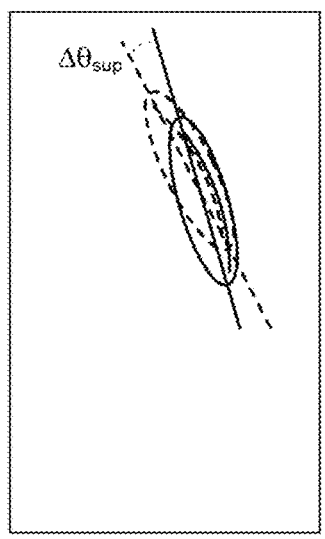
FIG. 17 shows a graphic representation according to FIG. 16 based on the top halves of said theoretical lateral labels.

According to a second aspect, shown in FIG. 17, the computation of the orientation of the theoretical lateral label is based on the top half of the theoretical lateral label in order to obtain the corresponding angles θ1sup and θ2sup and the corresponding angular deviation Δθsup.

Figure 18:
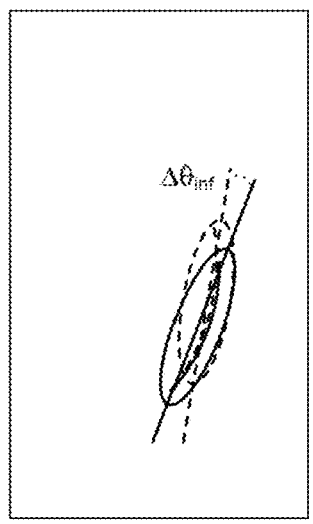
FIG. 18 shows a graphic representation of the labels according to FIG. 16 based on the bottom halves of said theoretical lateral labels.

According to a third aspect, shown in FIG. 18, the computation of the orientation of the theoretical lateral label is based on the bottom half of the theoretical lateral label in order to obtain the corresponding angles θ1inf and θ2inf and the corresponding angular deviation Δθinf.

For each of the three aspects, the deviations between the angles of orientation at T1 and at T2 are computed as indicated below:

$$\Delta\theta tot=|\theta 1tot-\theta 2tot|,$$

$$\Delta\theta sup=|\theta 1sup-\theta 2sup|,$$

$$\Delta\theta inf=|\theta 1inf-\theta 2inf|,$$

A range of the possible values of the optimal angle of orientation θopt is defined below:

Optimal range: [min (Δθtot, Δθsup, Δθinf)−0.2°; max (Δθtot, Δθsup, Δθinf)+0.2°].

The method for determining primary realignment parameters 1002 comprises a second step 150 of optimal realignment concerning the rotation and the translation of the Petri dish between the times T1 and T2, the center of the rotation being assimilated with the center of the Petri dish.

The step of optimal realignment makes it possible to determine, from the image acquired at the time T2, optimal primary realignment parameters comprising an angle of rotation and a translation vector in order to apply these parameters to the image acquired at the time T1 for the two images acquired to be able to be superimposed.

The determination of the optimal parameters is obtained by using a 2D cross-correlation function, as available in the Matlab™ software.

To estimate the optimal parameters, all the rotation angle values in the optimal range are tested with an interval of 0.1° of the image at T2 and the cross-correlation is computed between the image at T2 turned and the image at T1. Each resulting value represents the optimal translation for each rotation angle value in the optimal range. The maximum of these resulting values makes it possible to determine the optimal rotation and its associated optimal translation.

The second method of the global method of the invention relates to the secondary realignment or fine realignment 28. The second method can possibly be performed first, without the first method relating to the primary realignment having been performed previously.

Figure 19:
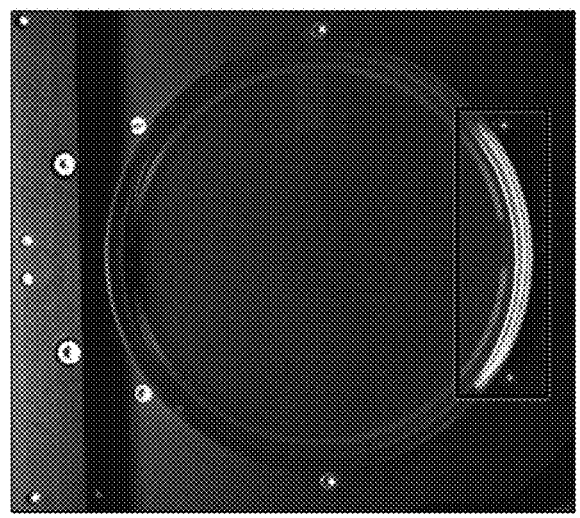
FIG. 19 shows an image of a Petri dish acquired at a time T1.

FIG. 19 shows a first image or initial image of a Petri dish, acquired by means of the image analysis system 10 at a time T1 before the incubation of the Petri dish for example.

Figure 20:
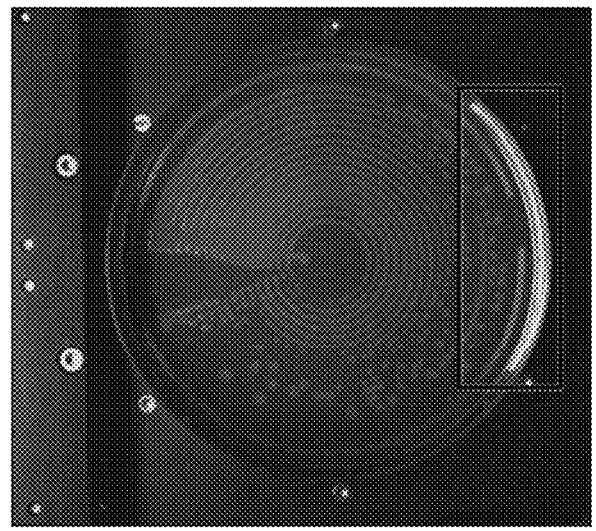
FIG. 20 shows an image of the Petri dish acquired at a time T2.

FIG. 20 shows a second image or final image of the Petri dish shown in FIG. 19 and acquired at a time T2 after the incubation of the Petri dish in the incubation device 20. As shown in FIG. 20, microorganism colonies are present in the Petri dish at the time T2.

Figure 21:
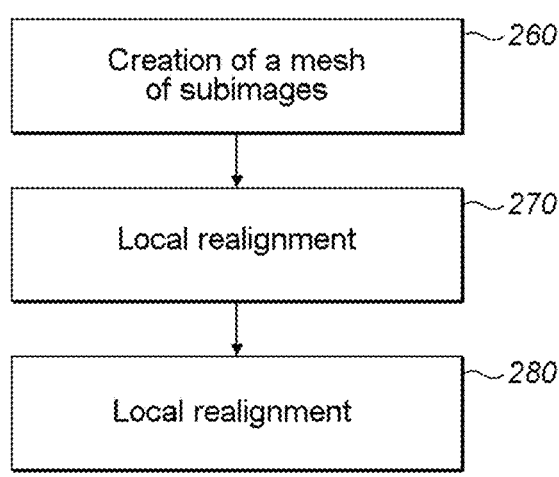
FIG. 21 shows a diagram of the steps concerning the secondary realignment method according to the embodiment of the invention.

As shown in FIG. 21, the secondary realignment method comprises a step 260 relating to the creation of a meshing of subimages in the initial image I1 acquired at the time T1 and of the final image I2 acquired at the time T2, a step 270 relating to a local realignment method and a step 280 relating to an global realignment method.

For the step 260 of creation of a meshing of subimages, an initial image I1 is gridded, as shown in FIG. 22, according to an initial meshing which comprises initial cells. FIG. 23 shows an example of an initial cell. The final image I2 is gridded as shown in FIG. 24 according to a final meshing which comprises final cells. FIG. 25 shows an example of a final cell. The dimension of an initial cell is greater than the dimension of a final cell.

As shown in FIG. 21, the secondary realignment method comprises a step 270 of local realignment concerning each pair of subimages obtained on completion of the step 260 described above.

Figure 26:
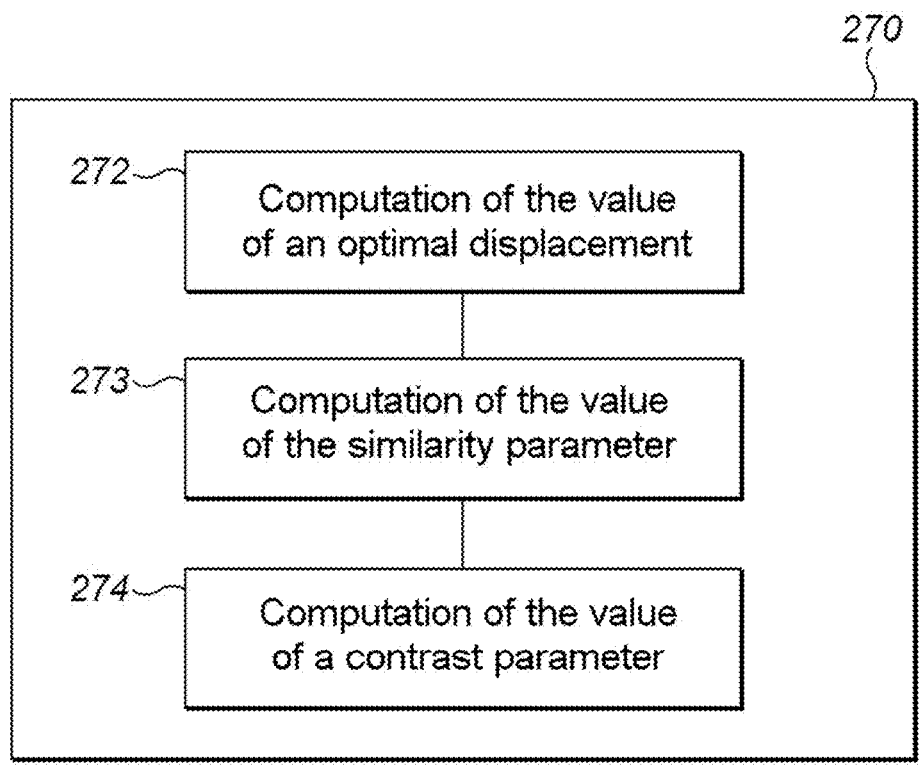
FIG. 26 shows a diagram of the steps relating to the local realignment method according to FIG. 21.

The local realignment step 270, shown in FIG. 26, comprises a substep 272 for computing the value of an optimal displacement between the two subimages concerned within the pair of subimages. The optimal displacement is estimated by considering the displacement of the final cell on the corresponding initial cell. In as much as the dimension of the final cell is smaller than the dimension of the initial cell, the displacement of the final cell is possible according to a displacement margin parameterized by the user. For each displacement, a value of a similarity parameter is computed in a step 273. This similarity parameter can be, for example, the measurement of distance or of mutual information. In the present invention, the similarity parameter corresponds to the correlation coefficient. For each displacement of the final subimage on the initial subimage, a value of the correlation coefficient is obtained. The maximum value of this correlation coefficient defines the optimal displacement for a pair of subimages.

The substep 274 makes it possible to compute the value of a contrast parameter between the two subimages considered in the pair of subimages realigned according to the optimal displacement estimated in the substep 272. The second contrast parameter makes it possible to evaluate the quantity of information present in each subimage of the pair of subimages. In the present invention, the value of the contrast parameter is computed as the standard deviation of the distance between the colors computed pixel-by-pixel according to the formula below:

$$\sigma_x = \sqrt{E[(X-E[X])^2]} = \sqrt{E[X^2]-E[X]^2}$$

The contrast parameter makes it possible to determine the subimages which are relevant for the subsequent computation in the global realignment method.

Figure 27:
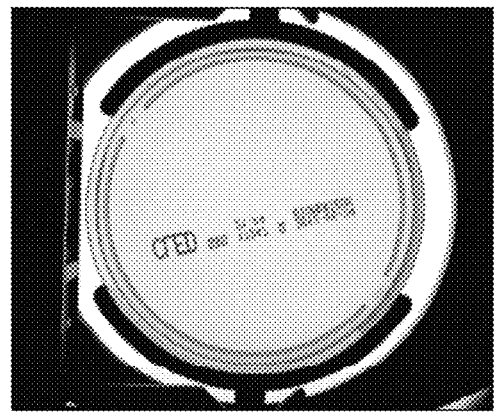
FIG. 27 shows an image of the Petri dish acquired at a time T1 according to the "backlight" acquisition condition.
Figure 28:
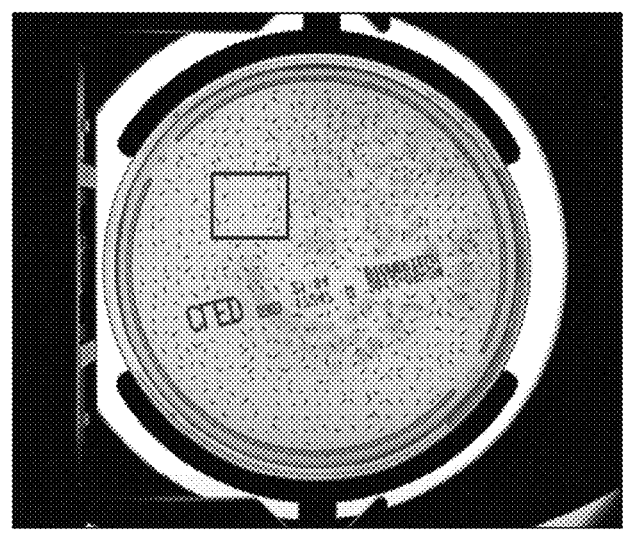
FIG. 28 shows an image of the Petri dish according to FIG. 27 acquired at a time T2 according to the "backlight" acquisition condition.
Figure 29:
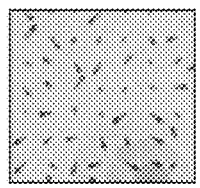
FIG. 29 shows in detail the content of the square represented in FIG. 28.

Thus, the step 270 makes it possible to obtain a set of local translational transformations between the initial image acquired at T1 shown in FIG. 27 and the final image acquired at T2 shown in FIG. 28 by vectors for each point of the meshing. FIG. 29 shows in detail the content of the square represented in FIG. 38. As shown in FIGS. 28 and 29, these local transformations are represented by vectors.

As shown in FIG. 21, the image realignment method according to the invention comprises a step 280 of global realignment. The step 280 makes it possible to use the results of the step 270 in order to deduce therefrom, for each pair of images I1 and I2, global realignment parameters.

The determination of a global transformation is performed on the basis, on the one hand, of the set of local transformations, that is to say of the translations and, on the other hand, of the similarity and contrast parameters for all the pairs of subimages.

The values of the similarity and contrast parameters make it possible to select the most relevant pairs of subimages. Thus, the corresponding most relevant local transformations can be deduced, for example, by applying a step of comparison with a threshold value.

Then, a global transformation is determined from most relevant local transformations for example by considering the mean, the median or the local transformation most frequently represented out of the local transformations.

As shown in FIG. 2, the global method according to the invention comprises a step 30 of prior determination of microorganism growth on the image I2 acquired at the time T=T2.

Figure 30:
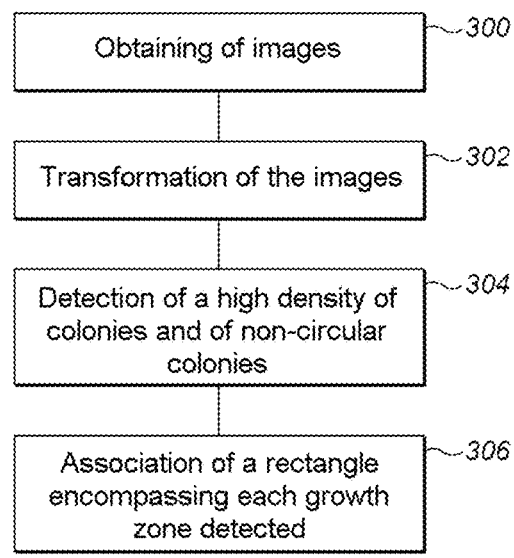
FIG. 30 shows a diagram of the steps relating to the method for determining preliminary growth of microorganisms according to FIG. 2.

The step 30 of FIG. 2 comprises the application a preliminary growth determination method in order to detect any microorganism growth in the Petri dish after incubation of said Petri dish. The prior growth determination method comprises a method for identifying potential growth zones a method for temporal analysis of said growth zones. As shown in FIG. 30, the preliminary growth determination method comprises a step 300 relating to the obtaining of one or more images of the Petri dish, on completion of the secondary realignment method, according to different acquisition conditions relating in particular to the illumination device 14.

The preliminary growth determination method also comprises a step 302 for creating a digital image from the images obtained in the step 300.

The preliminary growth determination method comprises a step 304 for detecting the presence of a high density of microorganism colonies and the microorganism colonies of non-circular form. Thus, the step 304 makes it possible to detect a microorganism growth zone, the form of said growth zone being variable. In order to facilitate the subsequent application of the computations, said growth zone is defined by means of a rectangle called "encompassing rectangle". The "encompassing rectangle" is centered on the growth zone and makes it possible to enlarge the surface of the growth zone according to a dimension determined in advance, for example 10 pixels around the growth zone.

The preliminary growth determination method next comprises a step 306 for associating a location element such as an encompassing rectangle with each growth element determined by the preliminary growth determination method.

Thus, the preliminary microorganism growth determination method makes it possible to determine whether microorganism colonies are present in the Petri dish.

In order to improve the results obtained from the preliminary determination method, a method for temporal analysis 40 of the microorganism growth is then applied in order to validate each rectangle encompassing a growth zone obtained upon the application of the preliminary microorganism growth determination method and thus obtain the indication of the actual growth of microorganisms in the Petri dish.

The temporal analysis method therefore considers the images obtained after the application of the optional primary realignment method and of the secondary realignment method and, for which, the application of the preliminary growth determination method has generated rectangles encompassing potential growth zones in the corresponding images.

According to the embodiment of the present invention, the initial images and the final images considered correspond to images acquired with the following three acquisition conditions: "backlight", "bottom" and "median".

In effect, each acquisition condition of the illumination device 14 allows a specific observation of the Petri dish. Thus, the illumination of "backlight" type makes it possible to observe, by transparency, the elements contained in the Petri dish.

The acquisition conditions of "bottom" and "median" type make it possible to observe the elements located on the surface of the agar culture medium in the Petri dish.

Figure 31:
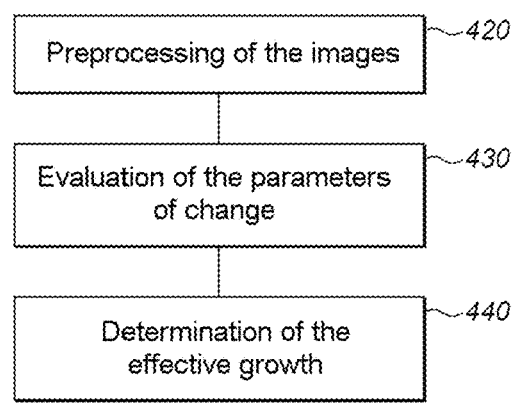
FIG. 31 shows a diagram of the steps of the temporal analysis method.

As shown in FIG. 31, the temporal analysis method comprises a step 420 for applying an image preprocessing method to the initial images and to the final images, a step 430 for evaluating criteria of change based on the initial images and the final images and a step 440 for determining actual microorganism growth.

Figure 32:
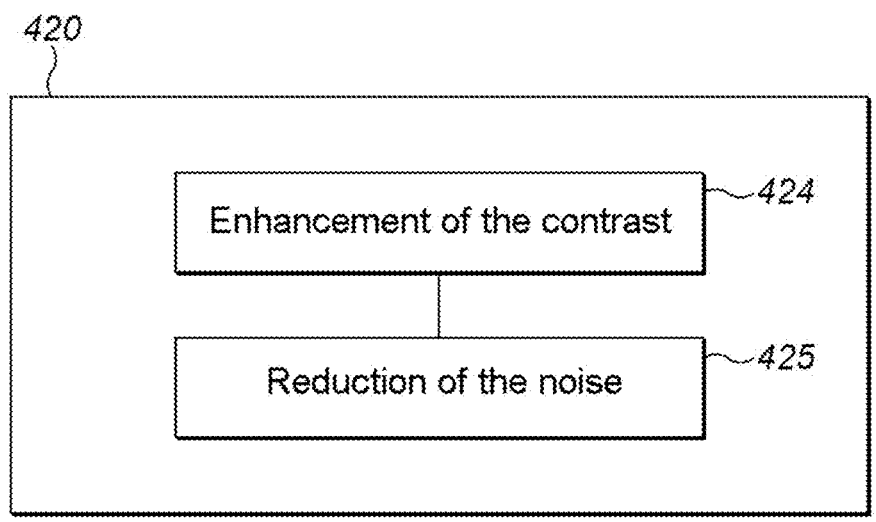
FIG. 32 shows a diagram of the steps relating to the image preprocessing method according to FIG. 31.

The step 420, relating to the image preprocessing method and shown in FIG. 32, comprises a substep 424 for improving the contrast in each zone relating to a rectangle encompassing said zone in the subimages. Thus, the substep 424 concerns the application of a method of adjusting contrast of an image such as histogram equalization known from the prior art. Thus, the images obtained after the step 424 contain different gray levels as shown in FIG. 33, according to the different illumination conditions, that is to say "backlight", "bottom" and "median".

The step 420 next comprises a substep 425 for reducing, in the image, the noise generated by increasing contrast. Thus, the substep 425 concerns the application of a median filter as known from the prior art, for example a filter for a 3×3 window.

Figure 33:
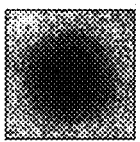
FIG. 33 shows examples of subimages acquired at T1 and at T2 according to the "backlight", "bottom" and "median" acquisition conditions after the application of a contrast adjustment method.
Figure 34:
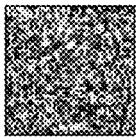
FIG. 34 shows examples of subimages acquired at T1 and at T2 according to the "backlight", "bottom" and "median" acquisition conditions after the application of a median filter.

Thus, on completion of the substep 425, the zones relating to the rectangles encompassing the potential growth zones contain transitions shown in FIG. 34, which are smoother and more uniform than the transitions of said zones shown in FIG. 33, on completion of the step 424.

As shown in FIG. 31, the temporal analysis method comprises a step 430 for determining, in the subimages, the value of at least one parameter of change.

According to a preferred embodiment of the invention, the value of two parameters of change must be determined for each set of subimages.

Figure 35:
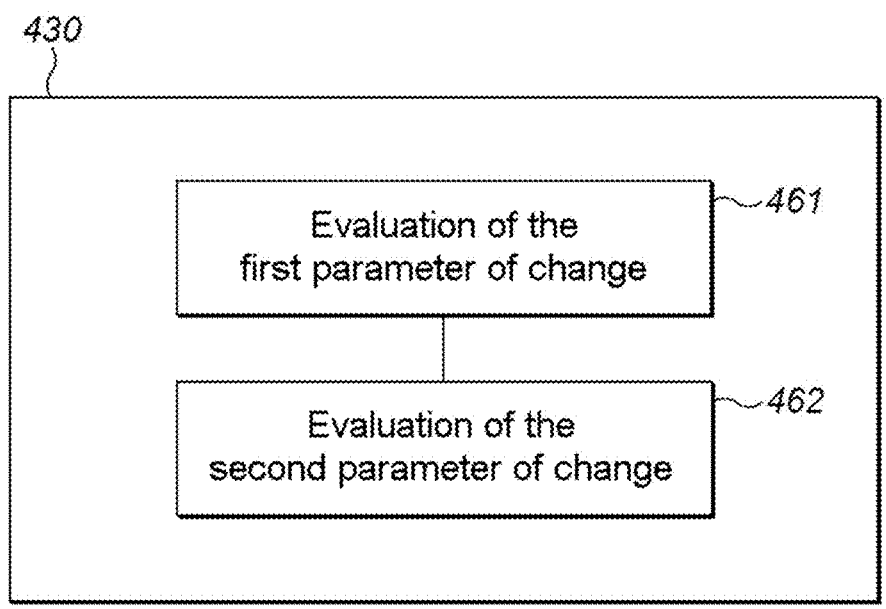
FIG. 35 shows a diagram of the steps relating to the evaluation of the first and second parameters of change according to FIG. 31.

The step 430 comprises a substep 461 shown in FIG. 35 and relating to the first parameter of change which makes it possible to characterize the change of the color in the subimages between the acquisition times T1 and T2. According to an embodiment of the invention, the first parameter of change corresponds to a contrast parameter which makes it possible to evaluate the global stability of the subimage between the acquisition times T1 and T2. According to an embodiment of the invention, the first parameter of change corresponds to a correlation parameter. The step 430 comprises a substep 462 shown in FIG. 35 and relating to the second parameter of change.

According to an embodiment of the invention, the contrast measurement method is based on the computation of the standard deviation, for example by means of the "std" function of the Matlab™ software, concerning the distances measured, for example by means of the "pdist" function of the Matlab™ software, between two pixels, and this is done for all the pixels located inside the encompassing rectangle:

$$C = \text{std}(\text{pdist}(\text{array}))$$

For the measurement of the contrast between voxels in the color subimage, the "array" variable corresponds to a column vector n×3.

For the measurement of the contrast between pixels in a subimage in gray levels, the "array" variable corresponds to a column vector n.

Figure 36:
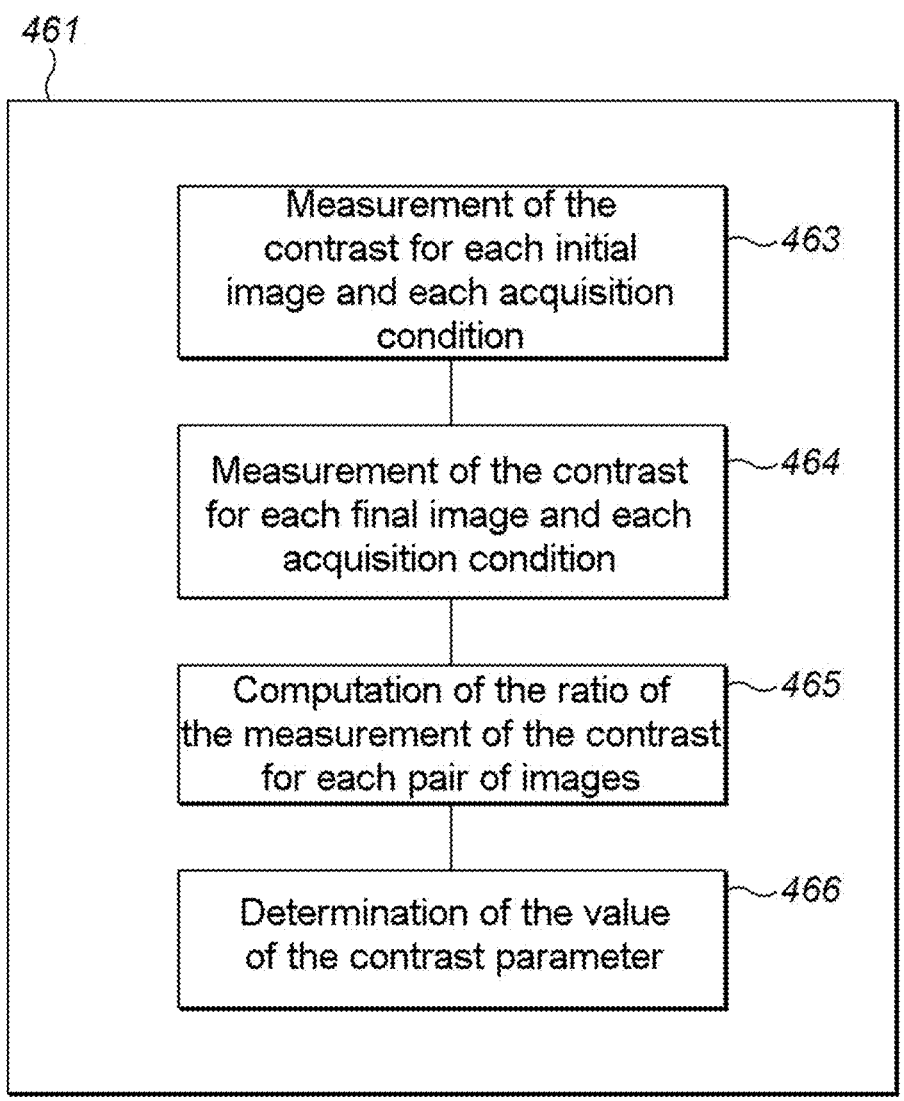
FIG. 36 shows a diagram of the steps relating to the evaluation of the contrast parameter according to an embodiment of the invention.

As shown in FIG. 36, the substep 461 relating to the computation of the contrast parameter comprises a plurality of steps based on the measurement of the contrast defined with the above equation C, according to an embodiment of the invention.

The first step 463 corresponds to the measurement of the contrast for each subimage of an initial image and for each of the "backlight", "bottom" and "median" illumination conditions.

The second step 464 corresponds to the measurement of the contrast for each subimage of a final image and for each of the "backlight", "bottom" and "median" illumination conditions.

The third step 465 corresponds to the computation of the ratios of the contrast measurements by considering, two-by-two, the measurements of contrast of a subimage at the times T1 and T2, for each illumination condition.

The fourth step 466 corresponds to the determination of the minimum value of the ratios obtained from the step 465 for determining the value of the contrast parameter.

The substep 461 corresponds to the application of the ContC equation below:

$$ContC = \min\left(\frac{C_{\{T_1 backlight\}}}{C_{\{T_2 backlight\}}}, \frac{C_{\{T_1 bottom\}}}{C_{\{T_2 bottom\}}}, \frac{C_{\{T_1 median\}}}{C_{\{T_2 median\}}}\right)$$

According to another embodiment of the invention, another equation, ContC_alt, can be applied by using the same contrast measurements:

$$ContC\_alt = \min\left(\frac{\min(C_{\{T_1 backlight\}}, C_{\{T_1 backlight\}})}{\max(C_{\{T_2 backlight\}}, C_{\{T_2 backlight\}})},\right.$$

$$\left.\frac{\min(C_{\{T_1 bottom\}}, C_{\{T_1 bottom\}})}{\max(C_{\{T_2 bottom\}}, C_{\{T_2 bottom\}})}, \frac{\min(C_{\{T_1 median\}}, C_{\{T_1 median\}})}{\min(C_{\{T_2 median\}}, C_{\{T_2 median\}})}\right)$$

The ContC_alt equation offers advantages over the ContC equation. In effect, the values obtained with the ContC_alt equation always lie within the range [0; 1]. In effect, for a stable element, that is to say an element which has not changed over time, the value obtained with the ContC_alt equation is close to 1, depending on an assessment margin that the user can set. Thus, for an assessment margin of 0.2, the value obtained for a stable element lies within the range [0.8; 1]. For a growth element, that is to say an element having changed over time, the value obtained with the ContC_alt equation is close to 0, depending on an assessment margin that the user can set. Thus, for an assessment margin of 0.2, the value obtained that has changed lies within the range [0; 0.2].

Figure 37:
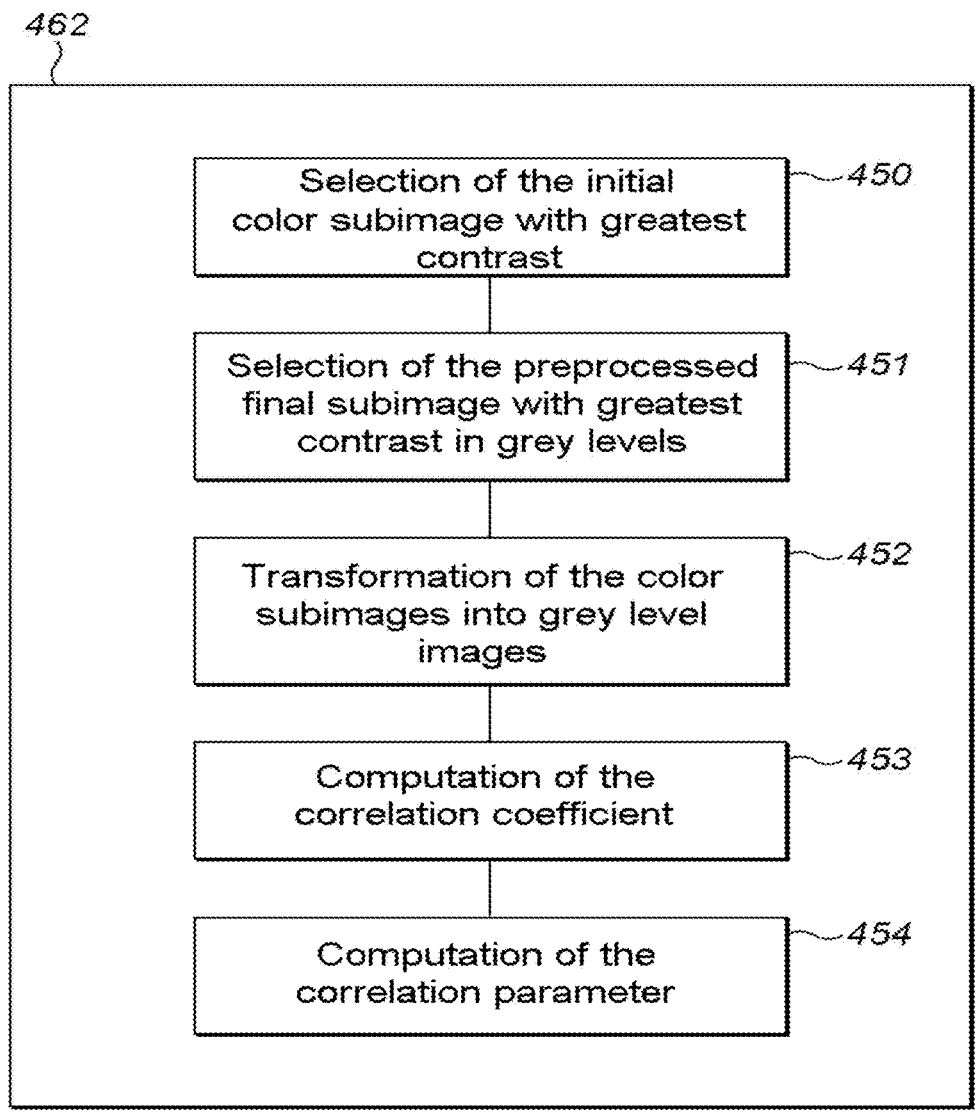
FIG. 37 shows a diagram of the steps relating to the evaluation of the correlation parameter according to an embodiment of the invention.

As shown in FIG. 37, the substep 462 comprises a plurality of steps. Thus, the first step 450 corresponds to the selection of the initial color subimage with the greatest contrast, out of the identical subimages obtained according to the three "backlight", "bottom" and "median" acquisition conditions.

The second step 451 corresponds to the selection of a corresponding preprocessed final image as obtained on completion of the steps 424 and 425.

The selection of the image with the greatest contrast in the steps 450 and 451 is based on the contrast measurement method described in the step 461.

The third step 452 comprises the transformation of the colored subimage into a subimage in gray levels.

The fourth step 453 comprises the computation of the correlation coefficient between the subimage acquired at T1 and the subimage acquired at T2, both in gray levels, by using the "corr 2" function of the Matlab™ software.

The fifth step 454 corresponds to the computation of the value of the correlation parameter which corresponds to the maximum value out of the two correlation coefficient values computed in the step 453 by means of the equation below:

$$\text{Corr } P = \max[\text{corr2}(T1\text{gray}, T2\text{gray}), \text{corr2}(T1\text{enhanced}, T2\text{enhanced})]$$

As shown in FIG. 31, the temporal analysis method comprises a step 440 for determining the actual microorganism growth in the Petri dish, at the end of a determined incubation period.

The objective of the step 440 is checking whether the element identified by a growth zone determined upon the application of the preliminary growth determination method in a subimage, in the step 30, actually corresponds to a growth element such as a microorganism colony or a set of microorganism colonies.

Figure 38:
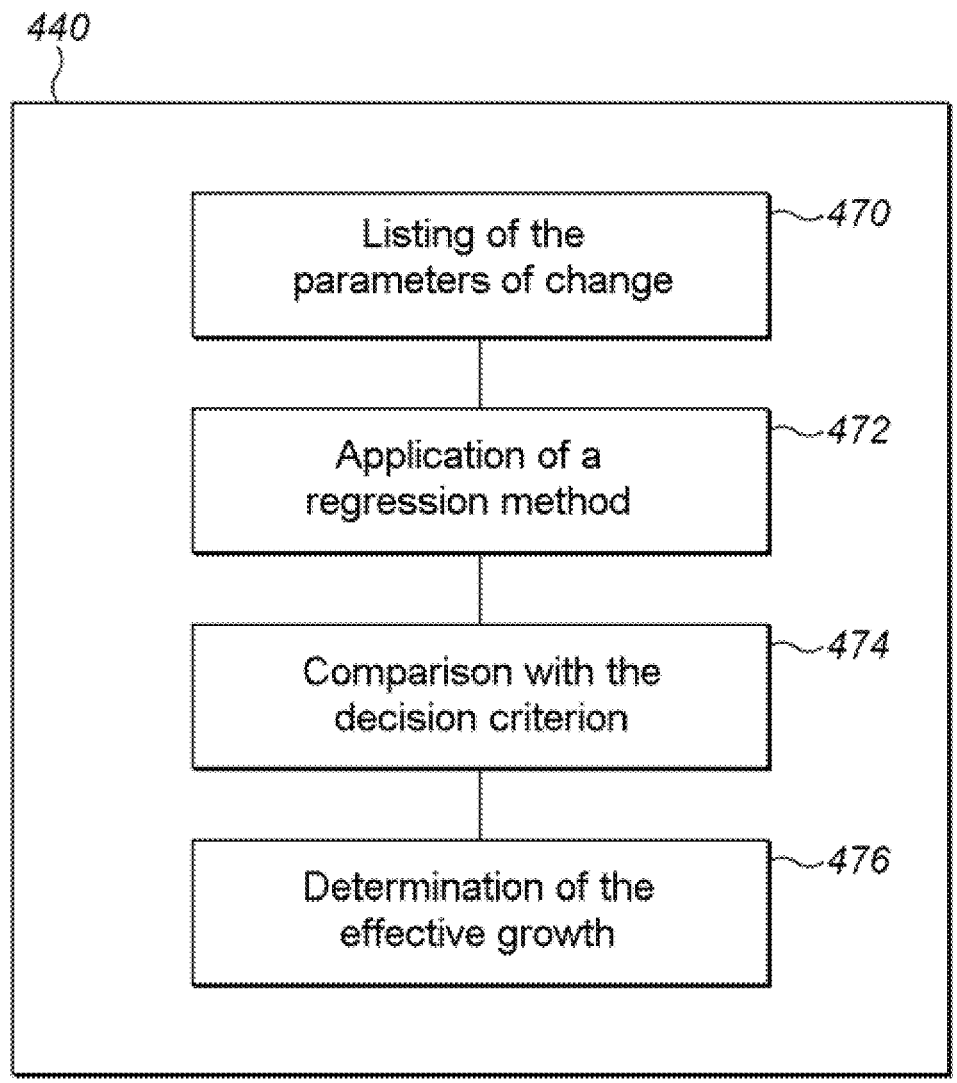
FIG. 38 shows a diagram of the steps relating to the determination of effective growth according to FIG. 31 according to an embodiment of the invention.

As shown in FIG. 38, the step 440 comprises a step 470 in order to list the different values obtained for the two parameters of change in the step 430. These values are associated with each rectangle encompassing the potential growth zones of the Petri dish for the acquisition time T2.

The step 440 then comprises a step 472 relating to the application of a logistical regression method. This method makes it possible to obtain a separation between two clusters of data to be discriminated on the basis of several parameters by means of a defined regression line. In the present invention, the logistical regression method used makes it possible to distinguish two clusters of data. The first cluster of data concerns the potential growth zones which are proven growth zones, that is to say positive zones. The second cluster of data relates to the potential growth zones which do not correspond to growth zones. These are negative zones. The logistical regression method in the present invention is based on two parameters, Corr P and ContC, according to the following equation:

$$CL = -10.3 \cdot \text{Corr } P - 9.65 \cdot \text{Cont}C\_v2 + 12.$$

Furthermore, for each value of correlation parameter Corr P and contrast parameter ContC, the equation P below makes it possible to determine a probability of presence of a growth element such as microorganism colonies from the value of CL defined above.

$$P = \frac{1}{1 + \exp(-CL)}$$

In order to classify the potential growth zones, the user can set a decision criterion on the values of P obtained.

Figure 39:
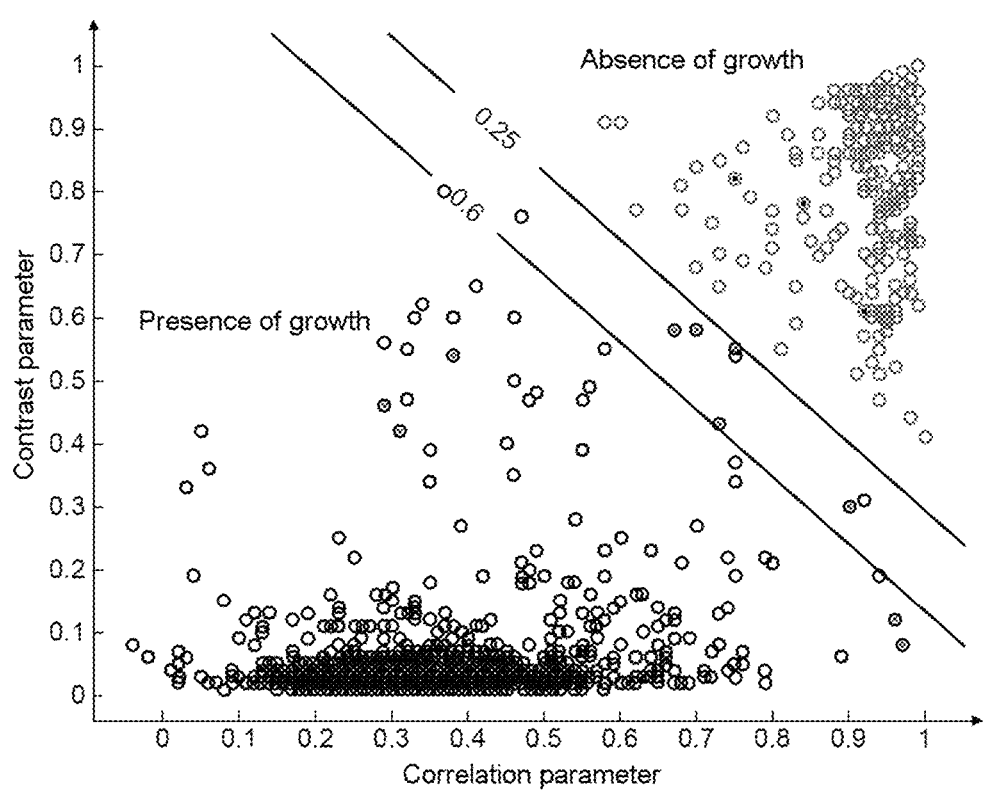
FIG. 39 shows a graphic representation of the microorganism growth as detected, as a function of the values of the contrast and correlation parameters.

According to an embodiment of the present invention shown in FIG. 39, the decision criterion P is set with the following values:

if P<0.25 then the potential growth zone corresponds to a stable element in time, thus the potential growth zone is not a growth zone, it is a so-called negative zone;

if P>0.6 then the potential growth zone corresponds to an element which changes over time and therefore the potential growth zone is a proven growth zone, it is a so-called positive zone;

if 0.25<P<0.6 then it is not possible to determine whether the potential growth zone corresponds to a stable element or to an element which changes over time, that is to say distinguishing between a so-called positive zone and a so-called negative zone is not possible.

The temporal analysis method then makes it possible to compare, in a step 474, the value of the local annotation with the decision criterion P, and therefore to search, for each potential growth zone of a final image, for the match with the corresponding initial image. Thus, in a step 476, the user can determine the absence or the presence of microorganism colonies in the Petri dish analyzed.

After the computation of the correlation and contrast parameters, the temporal analysis method makes it possible to determine whether the growth zone corresponds to an element that has changed or that has not changed over time.

When the growth zone corresponds to an element that has changed over time, the temporal analysis method makes it possible to confirm the validity of the growth zone as determined by the preliminary growth determination method. Thus, the growth zone actually corresponds to a microorganism growth.

When the growth zone corresponds to an element that has not changed over time, such as a defect linked to the material of the Petri dish, the temporal analysis method makes it possible to obtain a correction of the growth zone. Thus, the corrected growth zone indicates that the element observed in said growth zone does not correspond to a microorganism growth.

After the determination of the growth, the user has the possibility of identifying the nature of the microorganism colonies by means of an identification system (not shown).

The invention claimed is:

1. A method for determining microorganism growth in a biological sample, said biological sample being contained in an analysis container, said analysis container being subjected to an incubation of a determined duration, said method comprising the following steps:

acquiring a first plurality of initial images of the analysis container at a first acquisition time T1, before or during the incubation;

acquiring a second plurality of final images of the analysis container at a second acquisition time T2, during or after the incubation;

realigning each initial image of the first plurality of initial images acquired, with each corresponding final image of the second plurality of final images acquired;

locating at least one potential microorganism growth zone in at least one image of the second plurality of images acquired;

evaluating the content of the potential microorganism growth zone identified in order to determine the presence of microorganisms, wherein the realignment step further comprises a fine realignment step associated with the content of the analysis container, the fine realignment step comprising creating a mesh of subimages for each initial image and each final image.

2. The method for determining microorganism growth of claim 1, wherein the fine realignment step further comprises a step of locally realigning each pair of subimages.

3. The method for determining microorganism growth of claim 2, wherein the fine realignment step comprises a step of global realigning for which the global realigning parameters are deduced, for each pair of subimages, from said local realignment step.

4. The method for determining microorganism growth of claim 1, wherein the realignment step further comprises a rough realignment step associated with an identifier located on the analysis container.

5. The method for determining microorganism growth of claim 4, wherein the analysis container is a Petri dish, the identifier is a lateral label arranged on the lateral wall of the receptacle of said Petri dish, and wherein the rough realignment step further comprises a step of detecting the lateral label and a method for determining rough realignment parameters associated with the characteristics of the lateral label.

6. The method for determining microorganism growth of claim 5, wherein the step of detection of the lateral label further comprises a first step of detecting the edges of the Petri dish and a second step of locating the lateral label.

7. The method for determining microorganism growth of claim 1, wherein the step of locating at least one potential microorganism growth zone further comprises detecting a high density of microorganism colonies, detecting non-circular microorganism colonies and assigning a location element to said potential microorganism growth zone.

8. The method for determining microorganism growth of claim 1, wherein the step of evaluating the content of the potential growth zone identified further comprises determining the values of two parameters of change.

9. The method for determining microorganism growth of claim 8, wherein the two parameters of change comprise a correlation parameter and a contrast parameter.

10. A system for determining microorganism growth in a biological sample, said biological sample being contained in an analysis container, said analysis container being subjected to an incubation of a determined duration, said system comprising:
- an image capture device (12) for acquiring a plurality of images of the object to be analyzed at a first acquisition time T1, before or during the incubation, and at a second acquisition time T2, during or after the incubation;
- an illumination device (14) comprising one or more light sources for illuminating the analysis container;
- a control device (18) for controlling the application of the method for determining microorganism growth of claim 1, to determine the presence of microorganisms.

\* \* \* \* \*